(12) United States Patent
Acar

(10) Patent No.: US 12,226,121 B2
(45) Date of Patent: Feb. 18, 2025

(54) MULTI-HAIR GROOVING DEVICE

(71) Applicant: Levent Acar, Yeşilköy Bakrköy Istanbul (TR)

(72) Inventor: Levent Acar, Yeşilköy Bakrköy Istanbul (TR)

( * ) Notice: Subject to any disclaimer, the term of this patent is extended or adjusted under 35 U.S.C. 154(b) by 777 days.

(21) Appl. No.: 17/420,594

(22) PCT Filed: May 30, 2019

(86) PCT No.: PCT/TR2019/050402
§ 371 (c)(1),
(2) Date: Jul. 2, 2021

(87) PCT Pub. No.: WO2020/142022
PCT Pub. Date: Jul. 9, 2020

(65) Prior Publication Data
US 2022/0079623 A1    Mar. 17, 2022

(30) Foreign Application Priority Data
Jan. 3, 2019    (TR) .................. 2019/00054

(51) Int. Cl.
*A61B 17/3205*    (2006.01)
*A61B 17/34*    (2006.01)
*A61F 2/10*    (2006.01)
*A61B 17/00*    (2006.01)
*A61B 17/3211*    (2006.01)

(52) U.S. Cl.
CPC ...... *A61B 17/3468* (2013.01); *A61B 17/3205* (2013.01); *A61F 2/10* (2013.01); *A61B 2017/00752* (2013.01); *A61B 2017/00969* (2013.01); *A61B 17/3211* (2013.01)

(58) Field of Classification Search
CPC ............ A61B 17/3205; A61B 17/3209; A61B 17/32093; A61B 17/3211; A61B 17/3213; A61B 2017/00115; A61B 2017/00752; A61B 2017/00969; A61B 2034/2048; A61B 2090/067; A61F 2/10
See application file for complete search history.

(56) References Cited

U.S. PATENT DOCUMENTS 5,989,273 A * 11/1999 Arnold ................. A61B 17/322
606/167
6,887,250 B1 * 5/2005 Dority ............... A61B 17/3213
30/305

(Continued)

FOREIGN PATENT DOCUMENTS

| CN | 105615950 A | 6/2016 |
|---|---|---|
| WO | WO-2008115526 A2 | 9/2008 |
| WO | WO-2010104718 A1 | 9/2010 |

*Primary Examiner* — Diane D Yabut
*Assistant Examiner* — Christian D Knauss
(74) *Attorney, Agent, or Firm* — Intellectual Property Law Group LLP

(57) ABSTRACT

A multi-hair grooving device for use in obtaining natural results in hair transplantation. The multi-hair grooving device accommodating a goniometer and a direction meter, a counter, palm-use and includes a linear motor, a motor driver, a laser, an audible buzzer, a microprocessor, a digital screen, an accelerometer and goniometer, buttons, a battery reader, a power center, an ion battery and a micro-blades insertion apparatus.

4 Claims, 6 Drawing Sheets

(56) References Cited

U.S. PATENT DOCUMENTS

| | | | | |
|---|---|---|---|---|
| 2001/0034534 A1* | 10/2001 | Transue | ............ | A61B 17/3211 606/186 |
| 2003/0097143 A1* | 5/2003 | Mittelstaedt | ....... | A61B 17/3211 606/172 |
| 2012/0158019 A1 | 6/2012 | Tenney | | |
| 2018/0325544 A1 | 11/2018 | Park | | |

* cited by examiner

MULTI-HAIR GROOVING DEVICE

TECHNICAL FIELD

The present invention is useful in obtaining natural results in hair transplantation; particularly, this invention relates to a multi-hair grooving device accommodating an accelerometer and goniometer, a counter and is ergonomically suited for palm-use.

BACKGROUND OF THE INVENTION

Hair loss is a very common problem that almost all people encounter in a certain period of their lives. Hair loss that progresses individually at different speeds begins with the retraction of the forehead hairline and the thinning of the hair in the frontal and upper regions, and may progress to the opening of the entire top region over the time. These hair losses that constitute a very important part of the physical appearance cause physical problems as well as serious psychological problems.

Hair transplantation is the process of transferring healthy hair on the back and sides of the head with no risk of loss to the regions of loss. One of the most important stages of hair transplantation is the grooving process. The assignment of the hair direction and the determination of the hair frequency are performed by the grooving process. If the compliance between the groove and the graft cannot be achieved, there shall be no chance for hair transplantation to be successful.

As every person has a different hairline, they also have different hair directions and angles. Hair grows in different angles and extend in different directions on each side of the head. The direction and angle of hair in the forehead are different, and are also different at the top of the head and at the neck.

In order to get the best result fully from the natural hair transplantation operation, it is necessary to open hair grooves according to the natural hair directions and angles of the patient. This process directly affects the naturalness of the operation. The growth of the hair in different directions due to the wrong opening of the grooves affects the naturalness to a great extent.

For the realization of natural hair transplantation, it is required to create the ideal hairline and to open the groove at the right angle and direction. In cases where the correct hairline cannot be created and the groove cannot be opened in the appropriate direction and angle, the hair transplantation deviates from being natural regardless of its frequency.

In the state of the art, an average of 3500 to 4500 grooves are opened for a patient and this process lasts for 90-120 minutes. In the process that is currently performed manually, the physician moves his hand 3500-4000 times up and down in the same plane by maintaining the same position and direction. In doing so, on one hand, the physician tries to maintain the direction and angle of the incisions, and on the other hand, pays attention not to overlap the incisions (grooves), but to be very close to each other, and counts the grooves that are opened to prevent unnecessary skin damage.

In the state of the art, opening grooves larger than required may cause permanent scars. In addition, opening of grooves smaller than required can cause the roots to be damaged, dislodged and lost due to the force applied during the insertion of the roots into the grooves in the transplantation stage. For this reason, all grooves must be opened at their correct dimensions.

SUMMARY OF THE INVENTION

According to the present invention, the multi-hair grooving device, ensures easiness in the grooving process that is extremely exhausting and requires high concentration. With the present invention, extra incisions is are not made unnecessarily on the skin when opening the grooves. By means of the angle and direction measurement ability of the multi-hair grooving device; the direction (right and left tilt) and the angle (horizontal or perpendicular) of the hair grooves being opened can be determined in order to achieve natural results in hair transplantation. In addition, the device does not damage the natural hair roots and it is possible to count the number of hair grooves opened toon the right and left parts of the head. The structural and characteristic specifications and all advantages of the invention will become more apparent by means of the following figures and the detailed explanations written through referring to these figures, and therefore, this evaluation should be made by considering these figures and the detailed explanation.

BRIEF DESCRIPTION OF THE DRAWINGS

FIG. 4a is the front view of the multi-hair grooving device according to an embodiment of the present invention.

FIG. 4b is a side view of the multi-hair grooving device as shown in FIG. 4a.

FIG. 4c is the rear view of the multi-hair grooving device as shown in FIG. 4a.

FIG. 6a is the front view of a multi-hair grooving device according to another embodiment of the present invention.

FIG. 6b is a side view of the multi-hair grooving device as shown in FIG. 6a.

FIG. 6c is the rear view of the multi-hair grooving device as shown in FIG. 6a.

LIST OF REFERENCES

Figure 1:
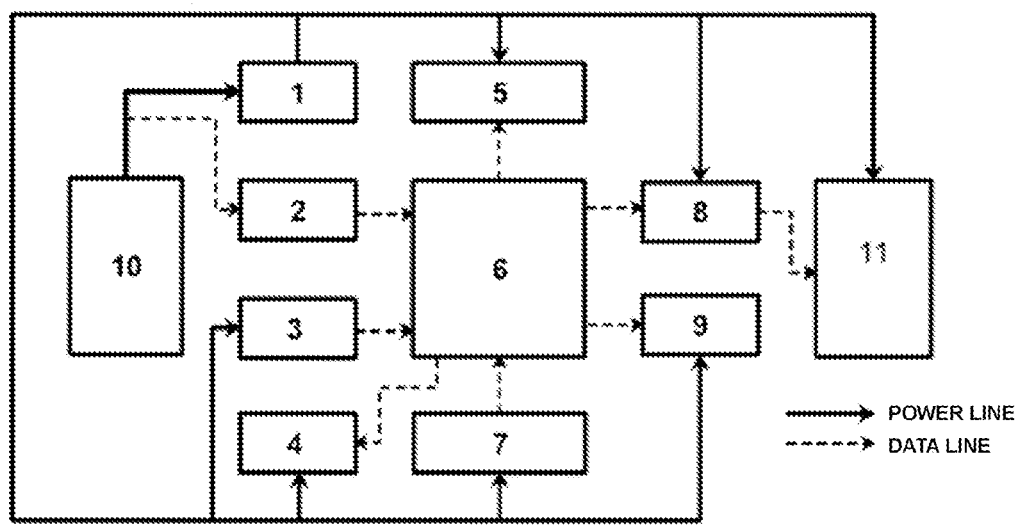
FIG. 1 is an overview of system components of a multi-hair grooving device.

1. Linear motor
2. Motor driver
3. Laser
4. Audible buzzer
5. Microprocessor

6. Digital screen
7. Accelerometer and goniometer
8. Buttons
9. Battery reader
10. Power center
11. Ion battery
20. Circuit board
30. Micro-blades insertion apparatus parts
32. Double point micro-blades
34. Triple point micro-blades
36. Single point micro-blade
40. Multi-hair grooving device
50. Faltenbalg (protective plastic bellow)
60. Multi-hair grooving device
65. Micro-blades insertion apparatus

DETAILED DESCRIPTION OF THE INVENTION

The multi-hair grooving device that is the subject of the invention is described in details below with no limiting effects.

Figure 2A:
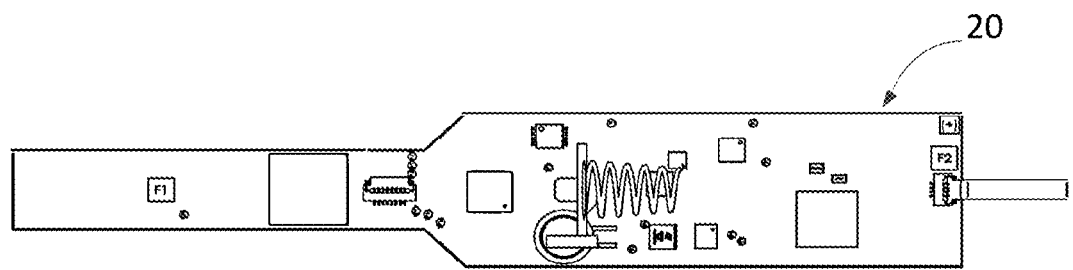
FIG. 2a is the top view of a circuit board of the multi-hair grooving device.
Figure 2B:
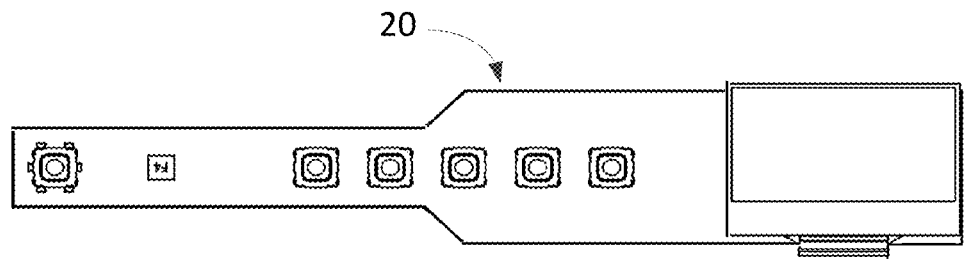
FIG. 2b is the bottom view of the circuit board of the multi-hair grooving device.

According to an embodiment of the invention, the multi-hair grooving device, is comprised of a linear motor (1); a motor driver (2), a laser (3), an audible buzzer (4), a microprocessor (5), a digital screen (6), an accelerometer and a goniometer (7), buttons (8), a battery reader (9), a power center (10), an ion battery (11) and a micro-blades insertion apparatus (65). FIG. 1 illustrates an overview of the system components of the multi-hair grooving device. FIGS. 2a-2b further show a top view and rear view respectively of a circuit board (20) of the multi-hair grooving device, according to an embodiment of the present invention.

The linear motor (1) is the motor that performs the back and forth movement of the multi-hair grooving device in the incision opening process in light of the data received from the microprocessor (5). In addition, it the microprocessor (5) performs the grooving procedure of the motor at the automatically adjusted depth as a result of the information received by being processed from the accelerometer and goniometer (7). By reducing the workload of the physician in the manual method, the device helps the physician to concentrate more on the aesthetic part of the hair grooves. At the same time, the number of grooves opened by the linear motor (1) can be counted automatically.

The motor driver (2) is the unit that achieves the required voltage and current values of the motor (1) that carries out the grooving procedure of the multi-hair grooving device through interpreting the information received from the microprocessor (5).

With a laser (3) integrated into the device, the device is enabled to indicate the incision part before the groove (incision) is opened. It is the unit that will ensure the marking of the grooving area before the groove is opened. Only the laser (3) is used for the purpose of indication with a light source. In this way, the grooves do not overlap. The incision on the existing healthy hair roots is prevented and thus the healthy hair roots are not damaged during the grooving procedure.

The audible buzzer (4) is the unit that emits signal sounds, warning and directing the user audibly during the transition between the menus of the multi-hair grooving device.

The microprocessor (5) is the central unit where all functions are processed. The microprocessor (5) interprets the information received from the accelerometer and goniometer (7) and displays the information on the digital screen (6). At the same time, the required commands are transmitted to the linear motor (1), the audible buzzer (4) and the laser (3) from this unit.

Figures 4A, 4B, 4C:
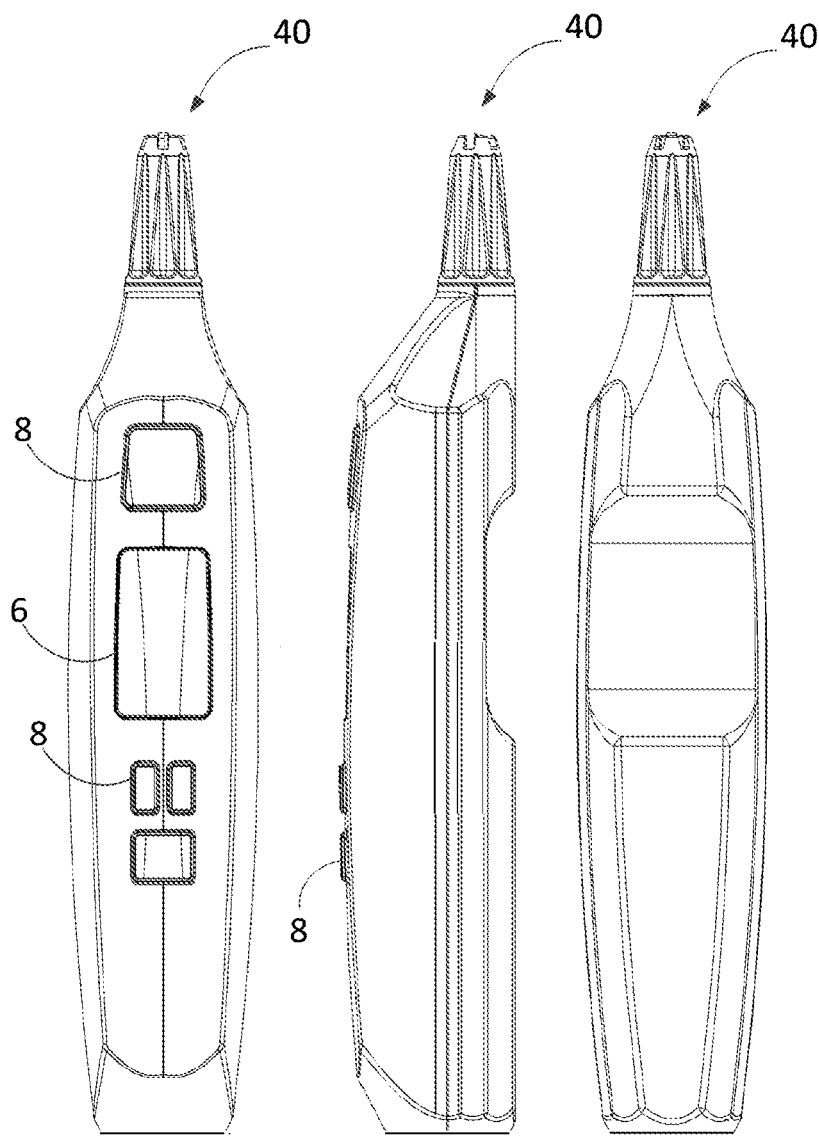

With the multi-hair grooving device (40) of the present invention, as illustrated in FIGS. 4a-4c, the physicians are able to get information instantly on the grooves opened with the digital screen (6). The number of grooves opened, the direction and angle information of the device (40), and the lithium ion battery (11) energy level can be monitored instantly on the digital screen (6). The digital screen (6) is the part through which the multi-hair grooving device (40) will interact with the user.

The accelerometer and goniometer (7) is the unit that reads the current angle and direction of the multi-hair grooving device. The information read from here is transmitted to the microprocessor (5).

Buttons (8) are the parts that allow the performance of various settings of the multi-hair grooving device (40) (incision speed, replacement of tip, changing the number of blades, etc.). At the same time, a single button (8) has been assigned for the grooving procedure. For the settings part, three (optionally five) buttons (8) have been allocated.

The battery reader (9) is the unit that reads the current voltage level of the lithium-ion battery (11) and transmits it to the microprocessor (5).

The power center (10) converts the energy received from the lithium ion battery (11) into a voltage level that is appropriate for the microprocessor (5), digital screen (6), buttons (8), audible buzzer (4), accelerometer and goniometer (7), motor driver (8) and linear motor (1).

The ion battery (11) is the power supply where the entire energy of the multi-hair grooving device (40) is provided. Lithium ion battery (11) has been used.

With the invention, the device (40) does not lose its angle when the patient or physician moves. In the case of changing the angle of the device (40), the tip of the device (40) is moved and calibrated automatically, so that the groove to be opened remains at the same depth. If the patient or the physician moves with the digital screen (6), the device (40) does not lose its direction. The exact angle of hair growth to the right or to the left as the patient's hair grows can be determined during the opening of the hair grooves. In addition, when opening the hair grooves, the depth can be set in mm from the digital screen (6).

Figures 3A, 3B:
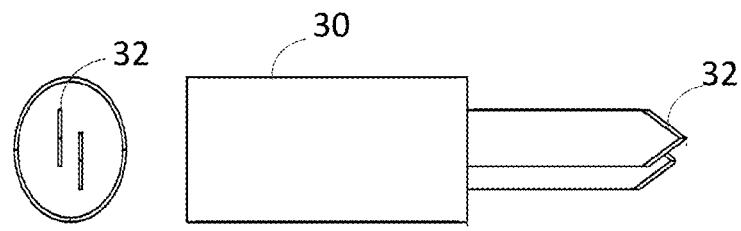
FIG. 3a is the front view of 2-point (double) micro-blades of the multi-hair grooving device.
FIG. 3b is a side view of 2-point (double) micro-blades of the multi-hair grooving device.
Figures 3C, 3D:
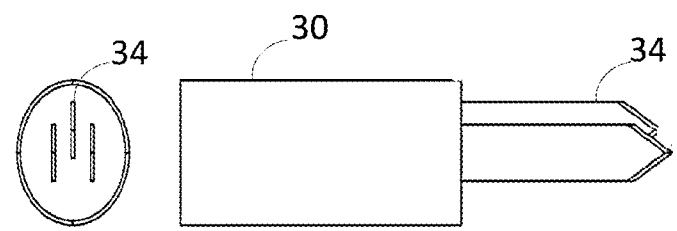
FIG. 3c is the front view of 3-point (triple) micro-blades of the multi-hair grooving device.
FIG. 3d is a side view of 3-point (triple) micro-blades of the multi-hair grooving device.
Figures 3E, 3F:
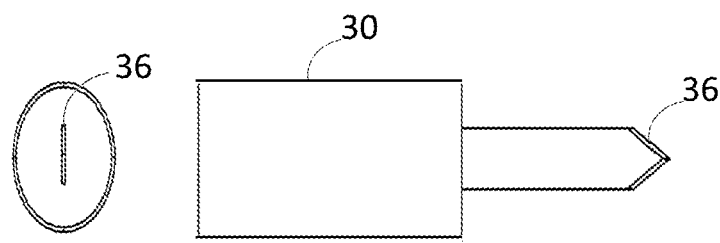
FIG. 3e is the front view of 1-point (single) micro blade of the multi-hair grooving device.
FIG. 3f is a side view of 1-point (single) micro blade of the multi-hair grooving device.
Figures 6A, 6B, 6C:
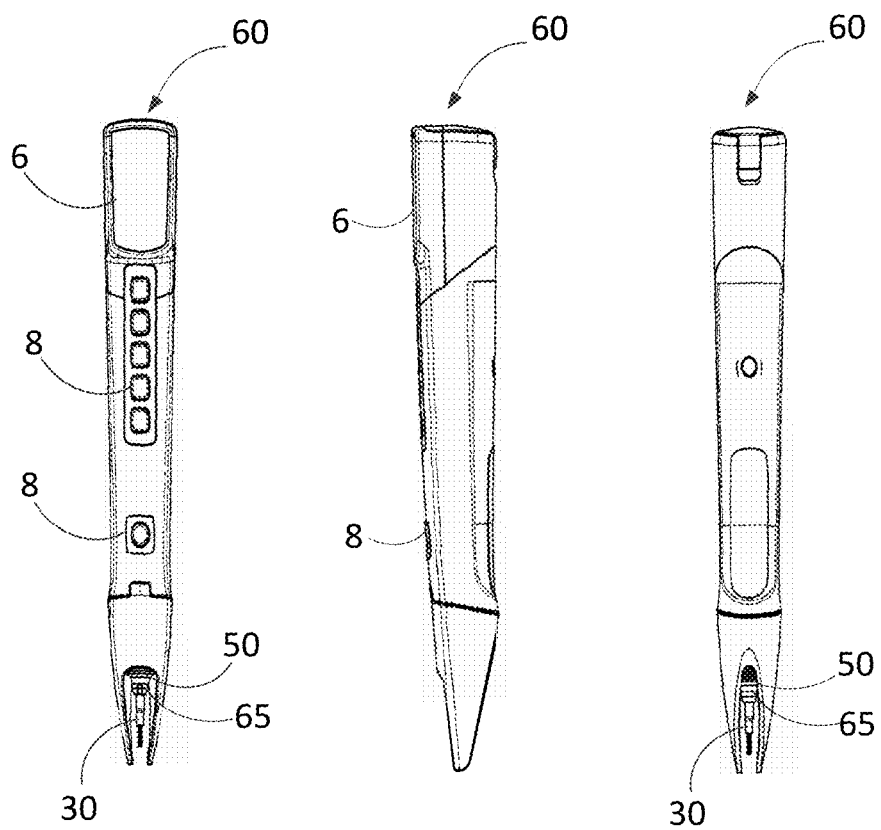

According to embodiments of the present invention, in the multi-hair grooving device (40, 60), the micro-blades insertion apparatus (65) fixes the micro-blades that are used for opening the hair grooves. The micro-blades insertion apparatus parts (30) can hold both a single blade (36) as seen in FIGS. 3e-3f, a double blade (32) as seen in FIGS. 3a-3b, and a triple blade (34) as seen in FIGS. 3d-3c. By means of the micro-blades insertion apparatus (65), the blades can be kept very close and very frequent (dense) grooves can be opened upon the request, or grooves in medium frequency can be opened by increasing the distance between the blades. In FIG. 6a, the front view of the multi-hair grooving device (60) according to an embodiment of the present invention is illustrated and shows the micro-blades insertion apparatus (65) from which the micro-blades insertion apparatus parts (30) extend out to secure the micro-blades. FIG. 6b further illustrates the side view of the multi-hair grooving device (60) and a rotation notch (not shown) is located on the micro-blades insertion apparatus (65), the rotation notch (0 degree and 90 degrees) specification, which ensures two different blade holding angles retained by the micro-blades insertion apparatus (65) seen in FIG. 6a allows the performance of both lateral and sagittal cut by means of using the micro blades as seen. FIG. 6c further illustrates the rear view of the device (60) seen in FIG. 6a and shows the combination of the micro-blades insertion apparatus (65) with the micro-blades insertion apparatus parts (30) and micro-blades.

In the case of multi-blade insertion with the micro-blades insertion apparatus (65), the blades stay as parallel to each other, but in the position known as zigzag or stair incision (as shown in FIGS. 3a and 3c).

Therefore, instead of opening the grooves fully side by side to get a natural hair transplantation result, opening at acertain distance can be ensured. Due to the specifications of the blades, incision in special geometric forms can be performed when they come side by side. At the same time, this apparatus can be used as a single-blade (see FIGS. 3e-3f), and there is an option of fixing more than one blade in a regular and parallel manner.

As can be seen in FIGS. 3a-3b, and 3c-3d, in the present invention, there is a difference of length between the blades in order to allow the blades to enter the skin evenly in the angled skin incision process. In this way, while the incisions are made at the previously determined angles, the incisions on the skin are ensured to have an equal depth.

In the multi-hair grooving device (40, 60) of the present invention there are different speed modes for opening the hair grooves. It allows the user to perform the operation at 5 different speed levels. The device can also operate manually by disabling all functions and can only perform groove counting in manual mode. When the grooves are opened during the hair transplantation with this multi-hair grooving device, it is possible to plan very frequent (dense), medium or rare hair transplantation according to a physician's request.

Figure 5:
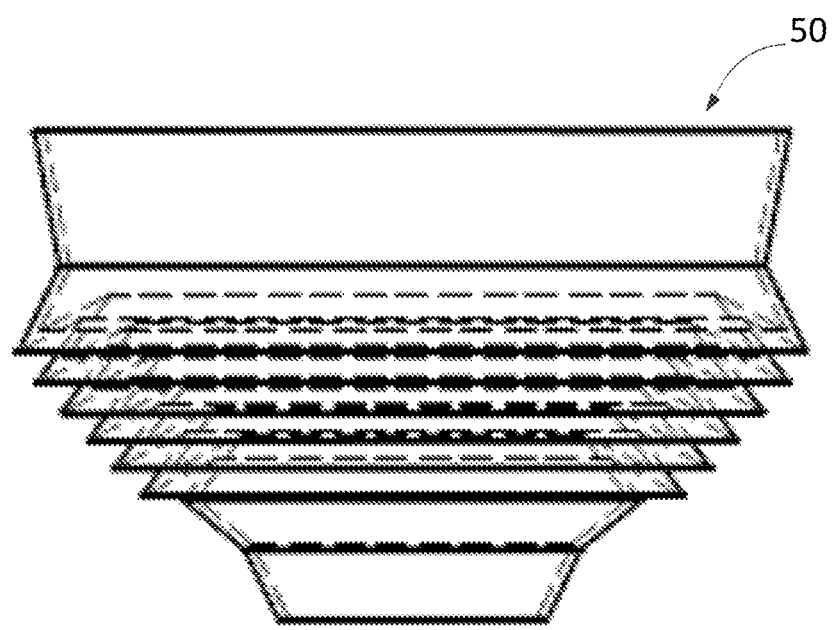
FIG. 5 is a side view of a faltenbalg (protective plastic bellow) of the multi-hair grooving device.

As shown in FIG. 5 and FIGS. 6a, 6c, a faltenbalg (protective plastic bellow) (50) can be attached on the blade. By means of this bellow (50), the entrance of the blood and cut fluids resulting during the operation into the device, as well as the sterilization fluids resulting during the sterilization into the device are prevented. By means of its flexible structure, the bellow (50) does not prevent the movements of the linear motor (1). The bellow (5) is disposable and can be replaced in every operation.

The present invention has ergonomics such that the device is able to be used by either the right hand or the left hand, making the device appropriate for opening the hair grooves by one hand, as the device settles comfortably into the palm. With this specification, the hand of the physician, who performs the operation, does not get tired during the operation and there are indents and details necessary for use with long-term performance.

While particular embodiments of the present invention have been shown and described, it will be obvious to those of ordinary skills in the art that based upon the teachings herein, changes and modifications may be made without departing from this exemplary embodiment(s) of the present invention and its broader aspects. Therefore, the appended claims are intended to encompass within their scope all such changes and modifications as are within the true spirit and scope of this exemplary embodiment(s) of the present invention.

The invention claimed is:

1. A multi-hair channel opening device that has different speed modes and is manually operable by deactivating all functions, and able to make hair transplantation planning, the multi-hair channel opening device comprising:
   a microprocessor where all functions are processed;
   an accelerometer and a goniometer, the accelerometer reads an instant angle and a direction of the device, and transmits readings to the microprocessor;
   a linear motor that performs back and forth movement of an incision process in response to data received from the microprocessor, the linear motor automatically performs the incision process at a depth set automatically by the linear motor in response to information received from the accelerometer and the goniometer, and the linear motor automatically counts a number of incisions made, hereinafter referred to as a number of opened channels, in skin of a patient during the incision process;
   a motor driver that provides a required voltage and current values of the linear motor by interpreting the data coming from the microprocessor, wherein the linear motor carries out movements of the incision process;
   a laser integrated into the device that allows the device to indicate where an incision is to be made and to mark a location of incision before the incision process;
   an audible buzzer emitting at least one audible signal to warn and direct a user, wherein the audible buzzer transmits the at least one audible signal during switches between menus;
   an ion battery that is a power source of energy;
   buttons that are exclusive for the incision process and ensure a performance of various settings;
   a battery reader for reading a current voltage level of the ion battery and transmitting the current voltage level to the microprocessor;
   a digital screen that allows a physician or the user to have instant information about opened channels, where the number of opened channels in the skin, a direction, a depth and an angle information of the device, and an energy level of the ion battery can be monitored instantly, wherein the digital screen serves to interact with the physician or the user;
   wherein the microprocessor interprets the information coming from the accelerometer and goniometer and displays the information on the digital screen, at the same time the microprocessor transmits required commands to the linear motor, the audible buzzer and the laser;
   a power center that converts the energy coming from the ion battery into a voltage level corresponding to the microprocessor, the digital screen, the buttons, the audible buzzer, the accelerometer and goniometer, the motor driver and the linear motor;
   and
   micro-blade insertion apparatus parts that hold micro-blades for making incisions wherein the micro-blade apparatus parts are capable of the following:
      holding more than one micro-blade at the same time,
      performing incision at a first arrangement by holding the micro-blades close together or at a second arrangement by increasing a distance between the micro-blades,
      keeping the micro-blades parallel to each other, but in a position that is-makes a zigzag or stair incision in the skin,
      performing incision in geometric forms when the micro-blades are brought together, and
      fixing one or more micro-blades side to side in a parallel manner.

2. The multi-hair channel opening device according to claim 1, wherein, in case the patient or the physician moves, a tip of the device automatically moves and is calibrated in order to prevent the device from losing a device angle and to keep the incision to be made at a same depth when the device changes the device angle.

3. The multi-hair channel opening device according to claim 1, further comprising a disposable protective plastic bellow, wherein the micro-blade insertion apparatus parts are able to hold single, double and triple blades, and are also able to ensure both lateral and sagittal cut.

4. The multi-hair channel opening device according to claim 1, wherein the multi-hair channel opening device has ergonomics for one handed use in a palm of either a right hand or a left hand.

* * * * *